United States Patent
Chu et al.

(10) Patent No.: US 10,150,080 B2
(45) Date of Patent: Dec. 11, 2018

(54) MICROORGANISM INCLUDING GENE ENCODING PROTEIN HAVING DEHALOGENASE ACTIVITY AND METHOD OF REDUCING CONCENTRATION OF FLUORINATED METHANE IN SAMPLE USING THE SAME

(71) Applicant: Samsung Electronics Co., Ltd., Suwon-si, Gyeonggi-do (KR)

(72) Inventors: Hunsu Chu, Seoul (KR); Joonsong Park, Seoul (KR); Jinhwan Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/332,525

(22) Filed: Oct. 24, 2016

(65) Prior Publication Data

US 2017/0114348 A1 Apr. 27, 2017

(30) Foreign Application Priority Data

Oct. 23, 2015 (KR) .................. 10-2015-0148032
Apr. 21, 2016 (KR) .................. 10-2016-0048960
Jun. 10, 2016 (KR) .................. 10-2016-0072704

(51) Int. Cl.
*C12N 9/14* (2006.01)
*B01D 53/70* (2006.01)
*B01D 53/84* (2006.01)

(52) U.S. Cl.
CPC ............. *B01D 53/70* (2013.01); *B01D 53/84* (2013.01); *C12N 9/14* (2013.01); *C12Y 308/01002* (2013.01); *C12Y 308/01005* (2013.01); *B01D 2251/95* (2013.01); *B01D 2255/804* (2013.01); *B01D 2257/2066* (2013.01)

(58) Field of Classification Search
None
See application file for complete search history.

(56) References Cited

U.S. PATENT DOCUMENTS

| | | | |
|---|---|---|---|
| 5,559,278 A | 9/1996 | Mouk et al. | |
| 5,637,499 A | 6/1997 | Turick | |
| 6,794,168 B1 | 9/2004 | Wong et al. | |
| 6,945,925 B2 | 9/2005 | Pooler et al. | |
| 2005/0027155 A1 | 2/2005 | Pooler et al. | |
| 2016/0333359 A1* | 11/2016 | Song ..................... | C12N 15/70 |
| 2017/0114348 A1 | 4/2017 | Chu et al. | |

FOREIGN PATENT DOCUMENTS

| | | |
|---|---|---|
| EP | 1433856 A1 | 6/2004 |
| EP | 1500704 A1 | 1/2005 |
| WO | WO 98/36080 A1 | 8/1998 |
| WO | WO 2008/016709 A2 | 2/2008 |

OTHER PUBLICATIONS

Chang et al. 1999 (In Vivo Screening of Haloalkane Dehalogenase Mutants; Bioorganic & Medicinal Chemistry 7: 2175-2181). (Year: 1999).*
Van der Ploeg et al. 1991 (Characterization of the Haloacid Dehalogenase from Xanthobacter autotrophicus GJ10 and Sequencing the dhlB gene; Journal of Bacteriology 173(24): 7925-7933). (Year: 1991).*
Keuning et al., Purification and Characterization of Hydrolytic Haloalkane Dehalogenase from *Xanthobacter autotrophicus* GJ10, *Journal of Bacteriology*, 163(2): 635-639 (1985).
European Patent Office, Extended European Search Report for Application No. 16202662.9, dated Mar. 22, 2017, 11 pages.
Csaki et al., Genes involved in the copper-dependent regulation of soluble methane monooxygenase of *Methyloccus capsulatus* (Bath): cloning, sequencing and mutational analysis, *Microbiology*, 149:1785-1795 (2003).
Janssen et al., Cloning of 1,2-Dichloroethene Degradation Genes of *Xanthobacter autrophicus* GJ10 and Expression and Sequencing of the dhlA Gene, *Journal of Bacteriology*, 171(12): 6791-6799 (1989).
Liu et al., Reaction Mechanism of Fluoroacetate Dehalogenase from *Moraxella* sp. B, *The Journal of Biological Chemistry*, 273(47):30897-30902 (1998).
Peterson et al., Putidaredoxin Reductase and Putidaredoxin, *The Journal of Biological Chemistry*, 265(11): 6068-6073 (1990).
Van Der Ploeg et al., Characterization of the Haloacid Dehalogenase from *Xanthobacter autrophicus* GJ10 and Sequencing of the dhlB Gene, *Journal of Bacteriology*, 173(24): 7925-7933 (1991).
European Patent Office, Extended European Search Report for Application No. 16169537.4, dated Feb. 13, 2017, 14 pages.
Beauvais et al., "Reactions of the diiron(IV) intermediate Q in soluble methane monooxygenase with fluoromethanes", *Biochemical and Biophysical Research Communications*, 338(1): 262-266 (2005).
Hyman et al., "Oxidation of Methyl Fluoride and Dimethyl Ether by Ammonia Monooxygenase in *Nitrosomonas europaea*", *Applied and Environmental Microbiology*, 60(8): 3033-3035 (1994).
European Patent Office, Office Action in European Application No. 16169537.4 (dated Jul. 26, 2018).

* cited by examiner

*Primary Examiner* — Mary Maille Lyons
(74) *Attorney, Agent, or Firm* — Leydig, Voit & Mayer, Ltd.

(57) ABSTRACT

Provided is a microorganism including a gene encoding a protein having a dehalogenase activity, a composition for using in reducing a concentration of fluorinated methane in a sample, the composition including the microorganism including the gene encoding the protein having the dehalogenase activity, and a method of reducing the concentration of fluorinated methane in the sample.

13 Claims, 6 Drawing Sheets

Specification includes a Sequence Listing.

MICROORGANISM INCLUDING GENE ENCODING PROTEIN HAVING DEHALOGENASE ACTIVITY AND METHOD OF REDUCING CONCENTRATION OF FLUORINATED METHANE IN SAMPLE USING THE SAME

CROSS-REFERENCE TO RELATED APPLICATIONS

This application claims the benefit of Korean Patent Application No. 10-2015-0148032, filed on Oct. 23, 2015, Korean Patent Application No. 10-2016-0048960, filed on Apr. 21, 2016 and Korean Patent Application No. 10-2016-0072704, filed on Jun. 10, 2016, in the Korean Intellectual Property Office, the disclosures of which are incorporated herein in their entireties by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 18,739 Byte ASCII (Text) file named "726633_ST25.TXT," created on Oct. 24, 2016.

BACKGROUND

1. Field

The present disclosure relates to a microorganism including a gene encoding a protein having a dehalogenase activity, a composition for using in reducing a concentration of fluorinated methane in a sample, the composition including the microorganism including the gene encoding the protein having the dehalogenase activity, and a method of reducing the concentration of fluorinated methane in the sample.

2. Description of the Related Art

The emission of greenhouse gases is a serious environmental problem which has accelerated global warming. Regulations aimed at reducing and preventing the emission of greenhouse gases have been tightened.

Among the greenhouse gases, fluorinated gases (F-gas) such as perfluorocarbons (PFCs), hydrofluorocarbons (HFCs), or sulfur hexafluoride ($SF_6$) show low absolute emission, but have a long half-life and a very high global warming potential, resulting in a significant adverse environmental impact. The amount of F-gas emitted by the semiconductor and electronics industries are a major causes of F-gas emission, and have exceeded the assigned amount of greenhouse gas emissions. Furthermore, the amount of F-gas emitted each year continues to increase. Therefore, costs required for degradation of greenhouse gases and greenhouse gas emission allowances are increasing every year.

A pyrolysis or catalytic thermal oxidation process has been generally used in the decomposition of F-gas. However, this process has disadvantages of limited decomposition rate, emission of secondary pollutants, and high cost. To solve this problem, biological decomposition of F-gas using a microbial biocatalyst has been adopted. Microbial biocatalysts are expected to overcome the limitations of the known chemical decomposition process and to treat F-gas in more economical and environmentally-friendly manner.

Therefore, there is a need to develop new microorganisms and methods for the removal of fluorinated methane in a sample. This invention provides such a microorganism and method.

SUMMARY

One aspect of the invention provides a recombinant microorganism having a genetic modification that increases the activity of a dehalogenase enzyme, wherein the recombinant microorganism has increased dehalogenase activity compared to a parent strain of the recombinant microorganism. Also provided is a method of preparing the recombinant microorganism.

Another aspect of the invention provides a composition for use in reducing a concentration of fluorinated methane represented by $CH_nF_{4-n}$ (where n is an integer of 0 to 3) in a sample, the composition including the recombinant microorganism, in which the recombinant microorganism includes one or more exogenous genes encoding a protein or proteins having dehalogenase activity, and the recombinant microorganism has increased dehalogenase activity, compared to the parent strain of the recombinant microorganism.

Still another aspect of the invention provides a method of reducing the concentration of fluorinated methane in a sample, the method including contacting the recombinant microorganism with the sample containing fluorinated methane represented by $CH_nF_{4-n}$ (where n is an integer of 0 to 3) to reduce the concentration of fluorinated methane in the sample.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
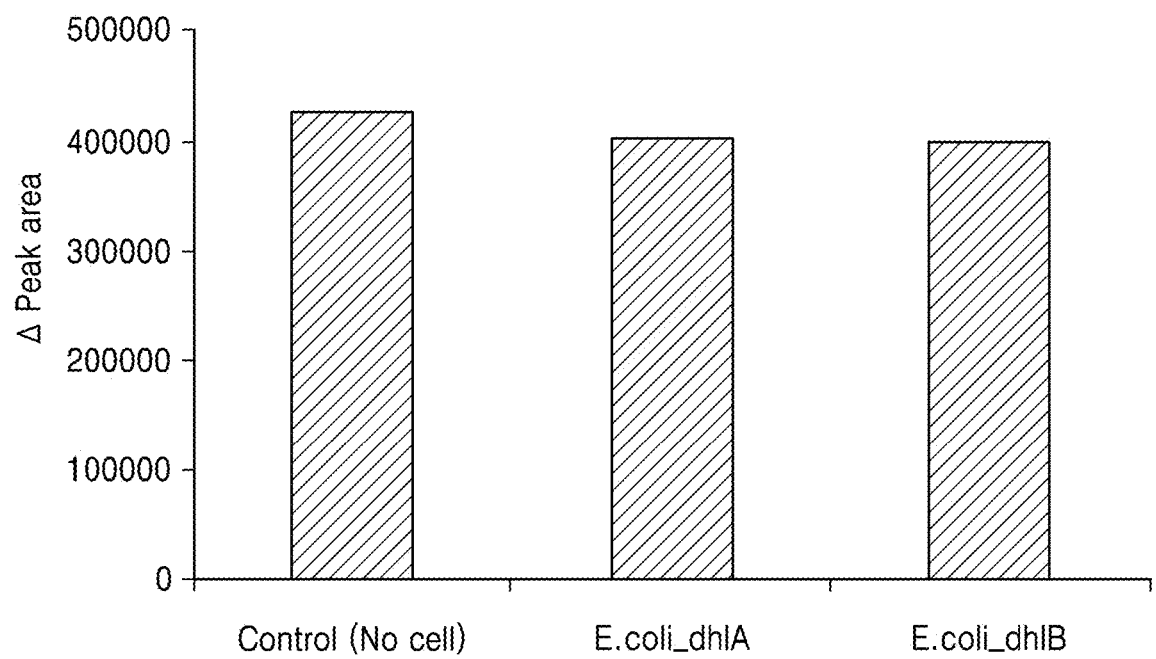
FIG. 1A shows the experimental results of decomposing fluoroform by recombinant *E. coli*.

The term "increase in activity" or "increased activity", as used herein, may refer to a detectable increase in an activity of a cell, a protein, or an enzyme. The "increase in activity" or "increased activity" may also refer to an activity level of a modified (e.g., genetically engineered) cell, protein, or enzyme that is higher than that of a comparative cell, protein, or enzyme of the same type, such as a cell, protein, or enzyme that does not have a given genetic modification (e.g., original or "wild-type" cell, protein, or enzyme). For example, an activity of a modified or engineered cell, protein, or enzyme may be increased by about 5% or more, about 10% or more, about 15% or more, about 20% or more, about 30% or more, about 50% or more, about 60% or more, about 70% or more, or about 100% or more than an activity of a non-engineered cell, protein, or enzyme of the same type, i.e., a wild-type cell, protein, or enzyme, or a parent cell from which the genetically engineered cell is made.

A cell having an increased activity of a protein or an enzyme may be identified by using any method known in the art.

An increase in activity of an enzyme or a polypeptide may be achieved by an increase in the expression or specific activity thereof. The increase in the expression may be achieved by introduction of a polynucleotide encoding the enzyme or the polypeptide into a cell or by an increase in a copy number, or by a mutation in the regulatory region of the polynucleotide. The polynucleotide encoding the enzyme may be operably linked to a regulatory sequence that allows expression thereof, for example, a promoter, an enhancer, a polyadenylation region, or a combination thereof. The polynucleotide which is introduced externally or whose copy number is increased may be endogenous or exogenous. The endogenous gene refers to a gene which is included in a microorganism prior to introducing the genetic modification (e.g., a native gene). The exogenous gene refers to a gene that is introduced into a cell from the outside. The introduced gene may be homologous or heterologous with respect to the host cell. The term "heterologous" means that the gene is "foreign" or "not native" to the species of microorganism.

The "increase in the copy number" of a gene may be caused by introduction of an exogenous gene or amplification of the gene already existing in a microorganism, and may be achieved by genetically engineering a cell so that the cell is allowed to have a gene (e.g., extra copy of a gene) that does not exist in a non-engineered cell. The introduction of the gene may be mediated by a vehicle such as a vector. The introduction may be a transient introduction in which the gene is not integrated into a genome, or an introduction that results in integration of the gene into the genome. The introduction may be performed, for example, by introducing a vector into the cell, in which the vector includes a polynucleotide encoding a target polypeptide, and then, replicating the vector in the cell, or by integrating the polynucleotide into the genome.

The introduction of the gene may be performed by a known method, such as transformation, transfection, and electroporation. The gene may be introduced via a vehicle. As used herein, the term "vehicle" or "vector" refers to a nucleic acid molecule that is able to deliver other nucleic acids linked thereto. Examples of the vector are a plasmid vector, a virus-derived vector, etc. A plasmid is a circular double-stranded DNA molecule linkable with another DNA. Examples of the vector may include a plasmid expression vector, and a virus expression vector, such as a replication-defective retrovirus, adenovirus, adeno-associated virus, or a combination thereof.

As used herein, the gene manipulation to be used may be performed by molecular biological methods known in the art.

The term "parent cell" refers to an original cell, for example, a non-genetically engineered cell of the same type as an engineered cell. With respect to a particular genetic modification, the "parent cell" may be a cell that lacks the particular genetic modification, but is identical in all other respects. Thus, the parent cell may be a cell that is used as a starting material to produce a genetically engineered cell having an increased activity of a given protein (e.g., a protein having a sequence identity of about 95% or more to dehalogenase such as (S)-2-haloacid dehalogenase). The same comparison is applied to other genetic modifications.

The term "gene", as used herein, refers to a nucleic acid fragment expressing a specific protein. A gene may include a regulatory sequence of a 5'-non coding sequence and/or a 3'-non coding sequence, or can be free of regulator sequences.

The term "sequence identity" of a polynucleotide or a polypeptide, as used herein, refers to a degree of identity between nucleotide bases or amino acid residues of sequences obtained after the sequences are aligned so as to best match in certain comparable regions. The sequence identity is a value that is measured by comparing two sequences in certain comparable regions via optimal alignment of the two sequences, in which portions of the sequences in the certain comparable regions may be added or deleted compared to reference sequences. A percentage of sequence identity may be calculated by, for example, comparing two optimally aligned sequences in the entire comparable regions, determining the number of locations in which the same amino acids or nucleotides appear to obtain the number of matching locations, dividing the number of matching locations by the total number of locations in the comparable regions (that is, the size of a range), and multiplying a result of the division by 100 to obtain the percentage of the sequence identity. The percentage of the sequence identity may be determined using a known sequence comparison program, for example, BLASTN (NCBI), BLASTP (NCBI), CLC Main Workbench (CLC bio), MegAlign™ (DNASTAR Inc), etc. Unless otherwise mentioned in the present disclosure, parameters used in the operation of the program are selected as follows: Ktuple=2, Gap Penalty=4, and Gap length penalty=12.

Various levels of sequence identity may be used to identify various types of polypeptides or polynucleotides having the same or similar functions or activities. For example, the sequence identity may include a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100%.

The term "genetic modification", as used herein, includes an artificial alteration in a constitution or structure of a genetic material of a cell.

Unless stated otherwise, percent composition (%) is expressed as w/w %.

An aspect of the invention provides a recombinant microorganism having a genetic modification that increases dehalogenase activity compared to a parent strain of the recombinant microorganism. The genetic modification may be to increase the copy number of one or more genes encoding the protein or proteins having the dehalogenase activity (e.g., a dehalogenase enzyme).

With regard to the microorganism, the dehalogenase is a type of enzyme that catalyzes the removal of a halogen (e.g., fluorine, chlorine, bromine, or iodine atom) from a substrate. The dehalogenase may, thus, catalyze the removal of a fluorine from a substrate. The dehalogenase may be chloroform reductive dehalogenase CfrA, tetrachloroethene reductive dehalogenase, dichloromethane dehalogenase, haloalkane dehalogenase, alkylhalidase, (S)-2-haloacid dehalogenase, (R)-2-haloacid dehalogenase, 2-haloacid dehalogenase (configuration-inverting), haloacetate dehalogenase, or a combination thereof.

The protein having the dehalogenase activity may have 50% or higher, 55% or higher, 60% or higher, 65% or higher, 70% or higher, 75% or higher, 80% or higher, 85% or higher, 90% or higher, 95% or higher, 96% or higher, 97% or higher, 98% or higher, or 99% or higher sequence identity to an amino acid sequence of SEQ ID NO: 1 or 2. The protein having the dehalogenase activity may have the amino acid sequence of SEQ ID NO: 1 or 2. The protein having the amino acid sequence of SEQ ID NO: 1 may be classified into haloalkane dehalogenase. The protein having the amino acid sequence of SEQ ID NO: 1 may be an enzyme that catalyzes production of primary alcohol and halide from 1-haloalkane and water as substrates. The protein having the dehalogenase activity may be an enzyme belonging to EC 3.8.1.5. The protein having the amino acid sequence of SEQ ID NO: 2 may be classified into (S)-2-haloacid dehalogenase. Further, the protein having the amino acid sequence of SEQ ID NO: 2 may be an enzyme that catalyzes production of (R)-hydroxy acid and halide from (S)-2-haloacid and water as substrates. The protein having the (S)-2-haloacid dehalogenase activity may be an enzyme belonging to EC 3.8.1.2. One or more foreign genes encoding the protein having the dehalogenase activity may have nucleotide sequences of SEQ ID NOS: 3 and 4. Further, the gene may be codon-optimized with respect to the recombinant microorganism as a host cell. Codon optimization refers to production of a gene in which one or more endogenous codons are replaced with codons for the same amino acid but of preference in the corresponding host. The nucleotide sequences of SEQ ID NOS: 3 and 4 are genes encoding haloalkane dehalogenase (dhlA) and (S)-2-haloacid dehalogenase (dhlB) derived from *Xanthobacter autotrophicus*, respectively.

Chloroform reductive dehalogenase CfrA may have 50% or higher, 55% or higher, 60% or higher, 65% or higher, 70% or higher, 75% or higher, 80% or higher, 85% or higher, 90% or higher, 95% or higher, 96% or higher, 97% or higher, 98% or higher, 99% or higher, or 100% sequence identity to an amino acid sequence of SEQ ID NO: 6. CfrA may be encoded by a nucleotide sequence of SEQ ID NO: 5. CfrA is known to dechlorinate chloroform (CF) and 1,1,1-trichloroethane, but not 1,1-dichloroethane.

The recombinant microorganism may belong to the genus *xanthobacter, Escherichia, Agrobacterium, Corynebacterium, Rhodococcus, Mycobacterium*, or *Klebsiella*. The genus *Escherichia* may include *E. coli*. The genus *xanthobacter* may include *xanthobacter autotrophicus*.

With regard to the recombinant microorganism, the microorganism may include one or more, for example, 2 or more, 3 or more, 4 or more, 5 or more, 10 or more, or 50 or more foreign genes encoding the proteins having dehalogenase activity. When a plurality of genes is included in the microorganism, the genes may be of different types from each other (e.g., encoding different dehalogenase enzymes) or the plurality of genes may include multiple copies of the same gene. The genes may be integrated into the genome of the microorganism, or maintained independent of the genome.

The recombinant microorganism may reduce the concentration of fluorinated methane represented by $CH_nF_{4-n}$ (where n is an integer of 0 to 3) in a sample. The fluorinated methane may be reduced by introducing a hydroxyl group to carbon of the fluorinated methane by action of the protein on C—F or C—H bond thereof or by accumulating the fluorinated methane inside the cell of the microorganism. Further, the fluorinated methane may be reduced by cleaving of C—F bonds of $CH_nF_{4-n}$ converting of $CH_nF_{4-n}$ into other materials, or intracellular accumulating of $CH_nF_{4-n}$. The sample may be in a liquid or gas state. The sample may be industrial waste water or waste gas. The sample may be any sample including the fluorinated methane. The fluorinated methane may include $CF_4$, $CHF_3$, $CH_2F_2$, $CH_3F$, or a mixture thereof.

The recombinant microorganism may include an exogenous (e.g., foreign or native) gene encoding a protein having the dehalogenase activity of haloalkane dehalogenase (dhlA) from *Xanthobacter autotrophicus*, (S)-2-haloacid dehalogenase (dhlB) from *Xanthobacter autotrophicus*, or a combination thereof. The recombinant microorganism may be the genus *xanthobacter*, for example, *xanthobacter autotrophicus*. The recombinant microorganism may be the genus *Escherichia*, for example, *E. coli*.

With regard to the recombinant microorganism, the gene may be introduced into the microorganism by a general method known in the art, for example, transformation, electroporation, etc.

Another aspect provides a composition for use in reducing a concentration of fluorinated methane represented by $CH_nF_{4-n}$ (where n is an integer of 0 to 3) in a sample, the composition including the recombinant microorganism, in which the recombinant microorganism includes a genetic modification of increasing the dehalogenase activity, and the recombinant microorganism has increased dehalogenase activity, compared to a parent strain of the recombinant microorganism.

With regard to the composition, the recombinant microorganism, sample and fluorinated methane are the same as described above.

The term "reducing" includes reducing of a concentration of fluorinated methane in the sample by any amount, and includes complete removal of fluorinated methane from the sample. The sample may be a gas or a liquid. The composition or culture may further include a material that increases solubility of the fluorinated methane for a medium or a culture.

Still another aspect of the invention provides a method of reducing a concentration of fluorinated methane in a sample, the method including contacting the recombinant microorganism described herein with the sample containing $CH_nF_{4-n}$ (where n is an integer of 0 to 3) to reduce the concentration of fluorinated methane represented by $CH_nF_{4-n}$ (where n is an integer of 0 to 3) in the sample. All aspects of the recombinant microorganism and the sample containing fluorinated methane are the same as described above.

With regard to the method, the recombinant microorganism can be contacted with a sample in a liquid or solid phase. The contacting may be performed, for example, by contacting a culture of the microorganism cultured in a medium with the sample. The culturing may be performed under conditions where the microorganism may proliferate. The contacting may be performed in a sealed container (e.g., air-sealed, liquid-sealed, or both depending on the nature of the sample). The contacting may be performed when the growth stage of the microorganism is in an exponential phase or a stationary phase. The culturing may be performed under aerobic or anaerobic conditions. The contacting may be performed in the sealed container under conditions where the recombinant microorganism may survive. Thus, the contacting may be performed by using the viable recombinant microorganism. The conditions where the recombinant microorganism may survive may be conditions where the recombinant microorganism may proliferate or conditions where the recombinant microorganism may be allowed to be in a resting state.

The sample may be in a liquid or gas state. The sample may be industrial waste water or waste gas. The sample may be passively or actively contacted with the culture of the microorganism. The sample may be, for example, sparged into the culture of the microorganism. That is, the sample may be sparged into a medium or culture. The sparging may be sparging of the sample from the bottom to the top of the medium or culture. The sparging may include injecting of droplets of the sample.

With regard to the method, the contacting may be performed in a batch or continuous manner. The contacting may include, for example, contacting a fresh recombinant microorganism with the sample obtained in the reducing, in which the fresh recombinant microorganism includes a genetic modification of increasing dehalogenase activity, and the recombinant microorganism has increased dehalogenase activity compared to a parent strain of the recombinant microorganism. The contacting with the fresh microorganism may be performed twice or more, for example, twice, three times, five times, or ten times or more. The contacting may be continued or repeated until the concentration of fluorinated methane in the sample reaches a desired reduced concentration.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items.

Hereinafter, the present invention will be described in more detail with reference to Examples. However, these Examples are for illustrative purposes only, and the scope of the present invention is not intended to be limited by these Examples.

Example 1: Decomposition of Fluoroform by Dehalogenase-Introduced *E. coli*

(1) Introduction of Dehalogenase Gene into *E. coli*
(1.1) Introduction of dhlA and dhlB Genes Haloalkane dehalogenase (dhlA) and (S)-2-haloacid dehalogenase (dhlB) of *Xanthobacter autotrophicus* GJ10 were selected as enzymes having activity of decomposing fluoro-containing hydrocarbon. *Xanthobacter autotrophicus* GJ10 was purchased from German Collection of Microorganisms and Cell Cultures (DSMZ).

A gene encoding haloalkane dehalogenase(dhlA) (SEQ ID NO: 3) and a gene encoding (S)-2-haloacid dehalogenase (dhlB) (SEQ ID NO: 4) were inserted into NdeI and HindIII sites of a pET28a vector (Novagen), respectively to obtain a dhlA-expressing vector, pET28a_dhlA and a dhlB-expressing vector, pET28a_dhlB. These vectors were introduced into *E. coli*, respectively and then their introduction was confirmed by sequencing. The haloalkane dehalogenase-introduced *E. coli* and (S)-2-haloacid dehalogenase-introduced *E. coli* were designated as *E. coli*_dhlA and *E. coli*_dhlB, respectively.

(1.2) Introduction of CfrA Gene

A gene (SEQ ID NO: 5) encoding chloroform reductive dehalogenase (CfrA) of *Dehalobacter* sp. CF was inserted into EcoRI site of a pMALc2 vector (New England Biolabs Inc.) to obtain a CrfA-expressing vector, pMALc2-CfrA. This vector was introduced into *E. coli* BL21 Star, and its introduction was confirmed by sequencing. The CfrA gene-introduced *E. coli* was designated as *E. coli* BL21 star/pMALc2-CfrA.

(2) Decomposition of Fluoroform by Haloalkane Dehalogenase-Introduced *E. coli*

*E. coli*_dhlA and *E. coli*_dhlB obtained in section (1) were put at a density of $2{>}10^9$ cells/ml in a 10 ml M9 medium-containing-25 ml serum bottle a shaking reactor (Daihan Labtech), respectively and incubated together with $CHF_3$ at an initial concentration of 200 ppm (see FIG. 1A) or 600 ppm (performed only for *E. coli*_dhlA: see FIG. 1B) in a headspace volume for 48 hours at 30° C. under shaking at 230 rpm. Then, the amount of $CHF_3$ in the headspace was analyzed. For analysis, 0.5 ml was collected from the headspace using a syringe and injected into GC (Agilent 7890, Palo Alto, Calif., USA). The injected $CHF_3$ was separated through a CP-PoraBOND Q column (25 m length, 0.32 mm i.d., 5 um film thickness, Agilent), and changes in the $CHF_3$ concentration were analyzed by MSD (Agilent 5973, Palo Alto, Calif., USA). As a carrier gas, helium was used, and applied to the column at a flow rate of 1.5 ml/min. GC conditions were as follows: An inlet temperature was 250° C., an initial temperature was maintained at 40° C. for 2 minutes, and temperature was raised to 290° C. at a rate of 20° C./min. MS conditions were as follows: Ionization energy was 70 eV, an interface temperature was 280° C., an ion source temperature was 230° C., and a quadrupole temperature was 150° C. Unless otherwise mentioned, analysis of gas such as $CHF_3$, $CHCl_3$, and $CF_4$ was performed by using the above method. As a control group, 200 ppm of $CHF_3$ was incubated without the cells that is, *E. coli*_dhlA and *E. coli*_dhlB under the same conditions, and then measured. The M9 medium included 0.015 g/l of $CaCl_2$, 6 g of $Na_2HPO_4$, 3 g of $KH_2PO_4$, 0.5 g of NaCl, 1 g of $NH_4Cl$, 0.5 g/l of $MgSO_4$, and 2.0 g/l glucose.

FIG. 1A shows the experimental results of decomposing fluoroform by recombinant *E. coli*. As shown in FIG. 1A, *E. coli*_dhlA and *E. coli*_dhlB showed 6% and 7% reduction in the amount of fluoroform, respectively. This result of FIG. 1A indicates that haloalkane dehalogenase and (S)-2-haloacid dehalogenase have a fluoroform decomposition ability.

Figure 1B:
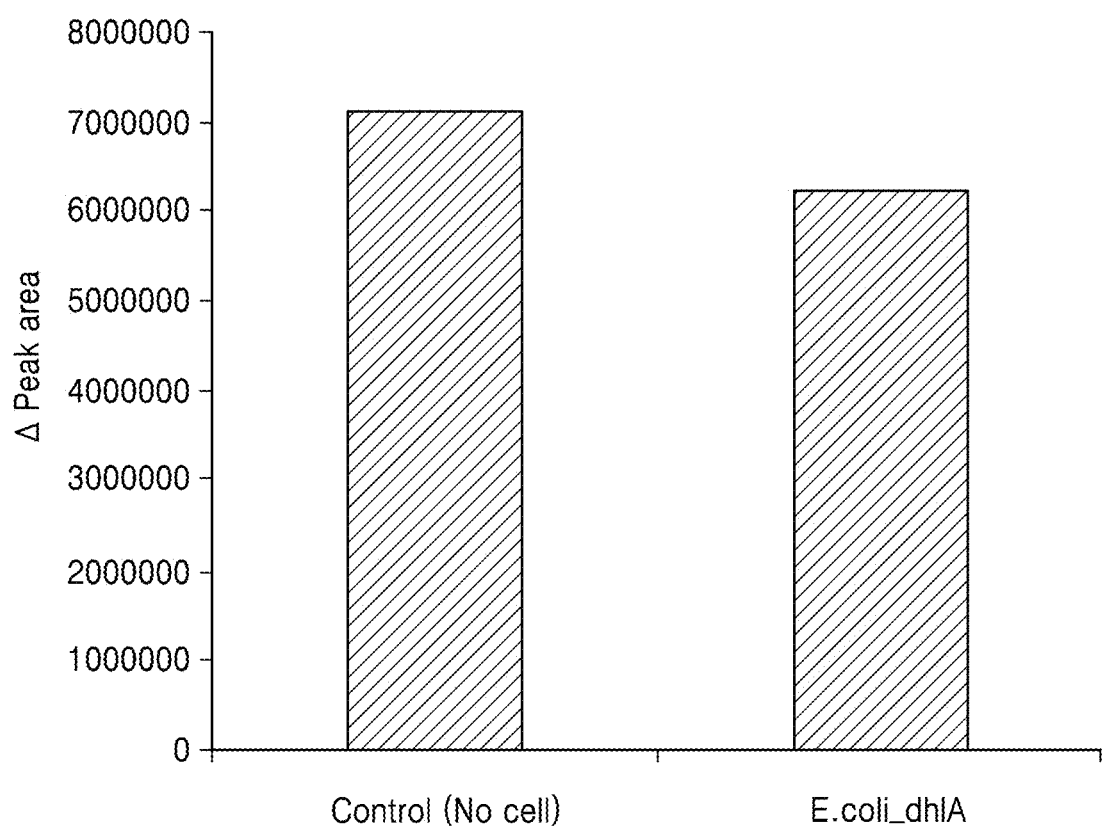
FIG. 1B shows the experimental results of decomposing fluoroform by haloalkane dehalogenase-introduced *E. coli*.

FIG. 1B shows the experimental results of decomposing fluoroform by haloalkane dehalogenase-introduced *E. coli*. As shown in FIG. 1B, *E. coli*_dhlA showed 12.4% reduction in the amount of fluoroform, compared to the control group. This result of FIG. 1B indicates that haloalkane dehalogenase-introduced *E. coli* is able to decompose a larger amount of trifluoromethane per hour as the initial concentration of trifluoromethane is higher.

(3) Decomposition of Perfluoromethane by Haloalkane Dehalogenase-Introduced *E. coli*

It is examined whether *E. coli* introduced with *Xanthobacter autotrophicus* GJ10-derived haloalkane dehalogenase has an ability to decompose perfluoromethane ($CF_4$).

A reduction in the $CF_4$ concentration was analyzed in the same manner as in section (2), except that *E. coli*_dhlA was used and $CF_4$ was added at a headspace concentration of 600 ppm.

Figure 2A:
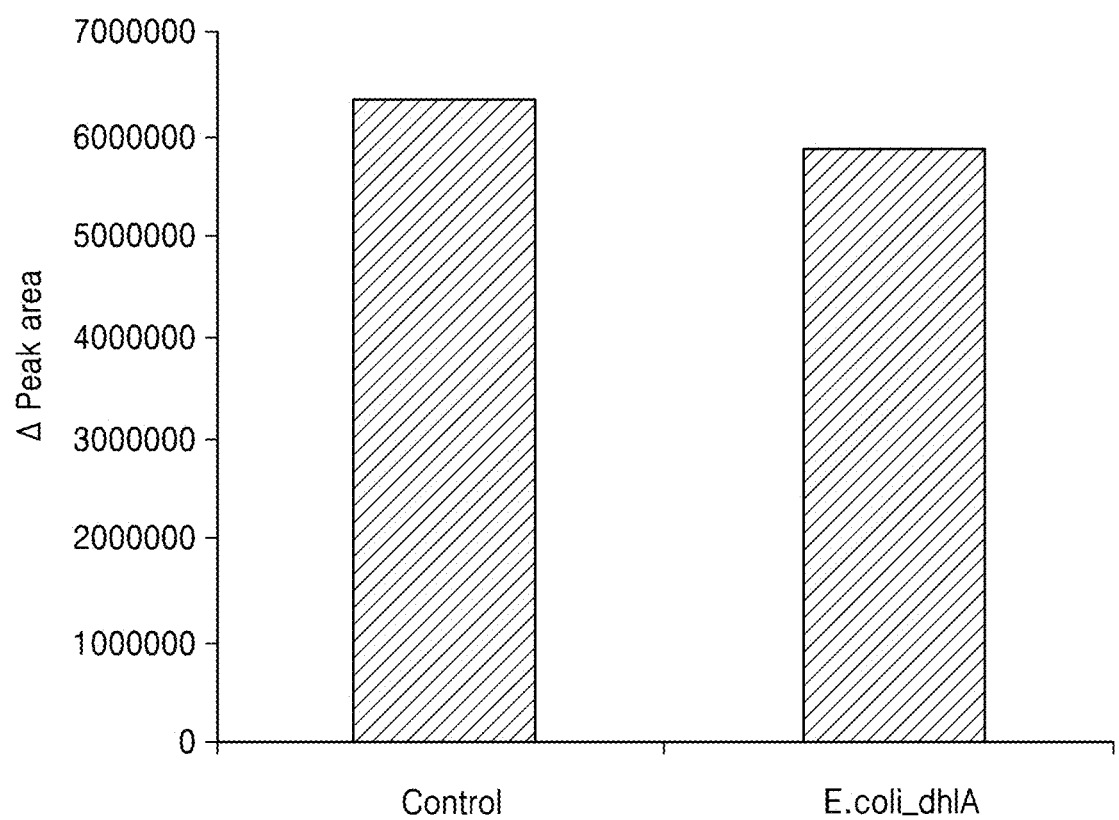
FIG. 2A shows the experimental results of decomposing perfluoromethane by haloalkane dehalogenase-introduced *E. coli*.

FIG. 2A shows the experimental result of decomposing perfluoromethane by haloalkane dehalogenase-introduced *E. coli*. As shown in FIG. 2A, *E. coli*_dhlA showed 7.6% reduction in the amount of perfluoromethane, compared to the control group. This result of FIG. 2A indicates that haloalkane dehalogenase-introduced *E. coli* has a perfluoromethane decomposition ability.

Further, *E. coli* BL21 star/pMALc2-CfrA prepared in section (1) was inoculated in a medium in a shaking incubator, and incubated in the presence of 0.2 mM IPTG and 1 µM cobalamin cofactor at 20° C. for 20 hours to induce expression of the CfrA gene. A cell pellet was obtained from a culture, and lysed in PBS buffer (Sigma-Aldrich Inc.) as a lysis solution to obtain a lysate. A crude extract was obtained from the lysate. Next, 2 mM Ti(III)-NTA, 2 mM methylviologen and 5 ml of the crude extract were added to a 25 ml serum bottle, and $CF_4$ was added at a headspace concentration of 1,000 ppm. The bottle was sealed and incubated at 30° C. for a predetermined time. A negative control (NC) was prepared in the same manner, except that E. coli BL21 star was used. As a result, 12% $CF_4$ was finally decomposed. A specific activity of the cell was 0.0044 umol/cell. Analysis of $CF_4$ was the same as described above.

Figure 2B:
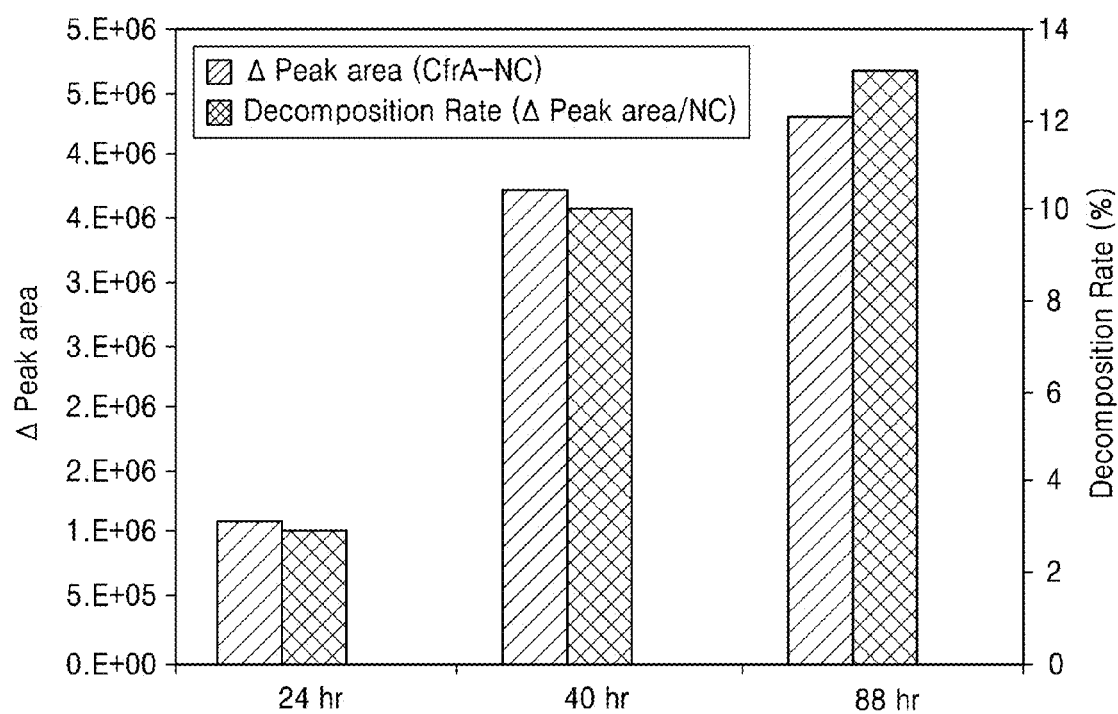
FIG. 2B shows changes in a concentration of $CF_4$ in a sample by *E. coli* BL21 star/pMALc2-CfrA, normalized using a negative control value, in which speak area represents CfrA area-negative control area, and decomposition rate (%) represents (Δpeak area/negative control)×100.

FIG. 2B shows changes in the $CF_4$ concentration in the sample by E. coli BL21 star/pMALc2-CfrA, which were normalized using a negative control value. In FIG. 2B, Δpeak area represents CfrA area-negative control area, and decomposition rate represents Δpeak area/negative control value.

Example 2: Decomposition of Tetrafluoromethane by Dehalogenase-Introduced Xanthobacter autotrophicus PCR was performed using a genomic sequence of Xanthobacter autotrophicus GJ10 purchased from German Collection of Microorganisms and Cell Cultures (DSMZ) as a template and a set of primers having nucleotide sequences of SEQ ID NOS: 7 and 8, and a dhlA gene (SEQ ID NO: 3) thus amplified was introduced into a pTSa vector using an In-Fusion HD Cloning Kit (Clontech) to prepare a pTSa_D-hlA vector (SEQ ID NO: 9) (ORF:2982-3914).

The vector thus prepared was transformed into X. autotrophicus GJ10 strain by electroporation, and a strain confirmed to have the dhlA gene was designated as Xantho_d-hlA. This strain was cultured in a 250 mL-plastic flask containing 50 mL of M9 medium at 30° C. under stirring at 230 rpm overnight.

Figure 3A:
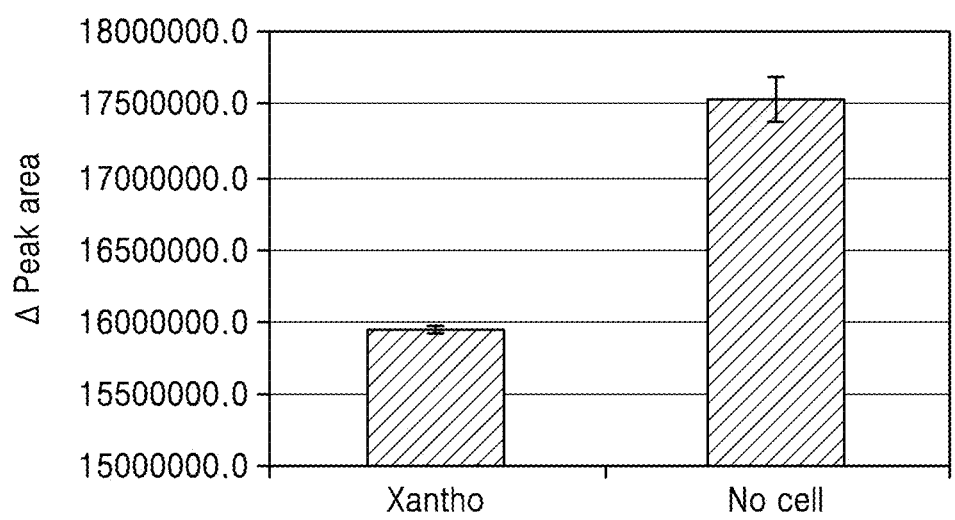
FIG. 3A shows decomposition of tetrafluoromethane by *X. autotrophicus* GJ10.
Figure 3B:
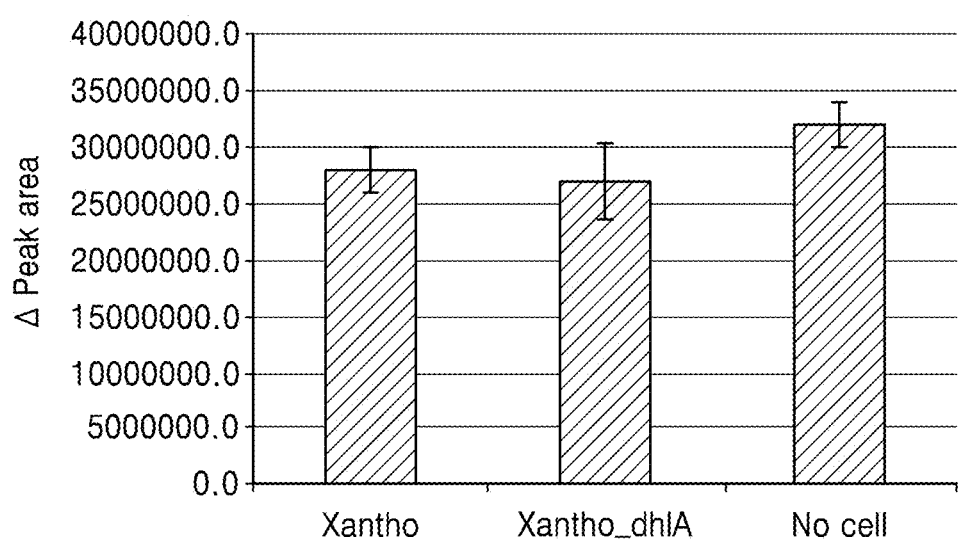
FIG. 3B shows decomposition of tetrafluoromethane by *X. autotrophicus* GJ10 Xantho and Xantho_dhlA strains.

A 25 ml-serum bottle containing 10 ml of $2×10^9$ cells/ml of Xantho_dhlA in the M9 medium and 600 ppm or 1000 ppm of $CF_4$ in the headspace was incubated in a shaking incubator (Daihan Labtech) under stirring at 230 rpm at 30° C. for 48 hours. Thereafter, a headspace concentration of $CF_4$ was analyzed. A control was prepared in the same manner, except that $CF_4$ was used in the headspace concentration of 600 ppm or 1000 ppm without cells and X. autotrophicus GJ10 was used under the same conditions. The results are given in FIGS. 3A and 3B. In FIGS. 3A and 3B, Xantho represents X. autotrophicus GJ10, Xantho_dhlA represents X. autotrophicus GJ10 Xantho_dhlA, and the vertical axis represents peak area, namely, Δpeak area.

FIG. 3A shows decomposition of tetrafluoromethane by X. autotrophicus GJ10. As shown in FIG. 3A, when the headspace concentration of $CF_4$ was 600 ppm, X. autotrophicus GJ10 decreased the amount of tetrafluoromethane by about 12.94%, compared to the control group.

FIG. 3B shows decomposition of tetrafluoromethane by X. autotrophicus GJ10 Xantho_dhlA. As shown in FIG. 3B, when the headspace concentration of $CF_4$ was 1000 ppm, X. autotrophicus GJ10 Xantho_dhlA and X. autotrophicus GJ10 decreased the amount of tetrafluoromethane by about 16.29% and 12.04%, compared to the control group, respectively. Therefore, X. autotrophicus GJ10 Xantho_dhlA showed remarkably efficient $CF_4$ decomposition, compared to X. autotrophicus GJ10.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant microorganism comprising a nucleic acid encoding chloroform reductive dehalogenase CfrA from the genus *Dehalobacter*, wherein the recombinant microorganism belongs to the genus *Xanthobacter, Agrobacterium, Corynebacterium, Rhodococcus, Mycobacterium, Klebsiella*, or *Escherichia*, and the recombinant microorganism has increased dehalogenase activity compared to a parent strain of the recombinant microorganism.

2. The recombinant microorganism of claim 1, wherein the microorganism comprises one or more nucleic acids comprising a promoter operably linked to a nucleic acid sequence encoding the CfrA, wherein one or more of the nucleic acids is heterologous to the microorganism.

3. The recombinant microorganism of claim 1, wherein the nucleic acid sequence encoding the CfrA comprises SEQ ID NO: 5.

4. The recombinant microorganism of claim 1, wherein the recombinant microorganism reduces a concentration of fluorinated methane in a sample contacted with the recombinant microorganism, wherein fluorinated methane is represented by $CH_nF_{4-n}$, where n is an integer of 0 to 3.

5. The recombinant microorganism of claim 4, wherein reducing the concentration of fluorinated methane comprises cleaving C—F bonds of the fluorinated methane, converting the fluorinated methane into other materials, or intracellular accumulation of the fluorinated methane.

6. The recombinant microorganism of claim 4, wherein the fluorinated methane is $CF_4$, $CHF_3$, or $CH_2F_2$.

7. A method of reducing the concentration of fluorinated methane in a sample, the method comprising contacting a recombinant microorganism of claim 1 with a sample containing fluorinated methane represented by $CH_nF_{4-n}$, where n is an integer of 0 to 3, to reduce the concentration of fluorinated methane in the sample.

8. The method of claim 7, wherein the recombinant microorganism is contacted with the sample in an air-sealed container.

9. The method of claim 7, wherein contacting the recombinant microorganism with the sample comprises culturing or incubating the recombinant microorganism with the sample.

10. The method of claim 7, wherein the recombinant microorganism proliferates in the air-sealed container.

11. The method of claim 7, wherein the fluorinated methane is $CF_4$, $CHF_3$, or $CH_2F_2$.

12. The method of claim 7, wherein the microorganism belongs to the genus *Escherichia*.

13. A method of preparing a recombinant microorganism of claim 1, the method comprising introducing into a microorganism a nucleic acid encoding chloroform reductive dehalogenase CfrA from the genus *Dehalobacter*, wherein the microorganism belongs to the genus *Xanthobacter, Agrobacterium, Corynebacterium, Rhodococcus, Mycobacterium, Klebsiella*, or *Escherichia*.

* * * * *

SEQUENCE LISTING

```
<160> NUMBER OF SEQ ID NOS: 9

<210> SEQ ID NO 1
<211> LENGTH: 311
<212> TYPE: PRT
<213> ORGANISM: Xanthobacter autotrophicus
```

<400> SEQUENCE: 1

```
Met Ile Asn Ala Ile Arg Thr Pro Asp Gln Arg Phe Ser Asn Leu Asp
  1               5                  10                  15

Gln Tyr Pro Phe Ser Pro Asn Tyr Leu Asp Asp Leu Pro Gly Tyr Pro
             20                  25                  30

Gly Leu Arg Ala His Tyr Leu Asp Glu Gly Asn Ser Asp Ala Glu Asp
         35                  40                  45

Val Phe Leu Cys Leu His Gly Glu Pro Thr Trp Ser Tyr Leu Tyr Arg
     50                  55                  60

Lys Met Ile Pro Val Phe Ala Glu Ser Gly Ala Arg Val Ile Ala Pro
 65                  70                  75                  80

Asp Phe Phe Gly Phe Gly Lys Ser Asp Lys Pro Val Asp Glu Glu Asp
                 85                  90                  95

Tyr Thr Phe Glu Phe His Arg Asn Phe Leu Leu Ala Leu Ile Glu Arg
            100                 105                 110

Leu Asp Leu Arg Asn Ile Thr Leu Val Val Gln Asp Trp Gly Gly Phe
        115                 120                 125

Leu Gly Leu Thr Leu Pro Met Ala Asp Pro Ser Arg Phe Lys Arg Leu
    130                 135                 140

Ile Ile Met Asn Ala Cys Leu Met Thr Asp Pro Val Thr Gln Pro Ala
145                 150                 155                 160

Phe Ser Ala Phe Val Thr Gln Pro Ala Asp Gly Phe Thr Ala Trp Lys
                165                 170                 175

Tyr Asp Leu Val Thr Pro Ser Asp Leu Arg Leu Asp Gln Phe Met Lys
            180                 185                 190

Arg Trp Ala Pro Thr Leu Thr Glu Ala Glu Ala Ser Ala Tyr Ala Ala
        195                 200                 205

Pro Phe Pro Asp Thr Ser Tyr Gln Ala Gly Val Arg Lys Phe Pro Lys
    210                 215                 220

Met Val Ala Gln Arg Asp Gln Ala Cys Ile Asp Ile Ser Thr Glu Ala
225                 230                 235                 240

Ile Ser Phe Trp Gln Asn Asp Trp Asn Gly Gln Thr Phe Met Ala Ile
                245                 250                 255

Gly Met Lys Asp Lys Leu Leu Gly Pro Asp Val Met Tyr Pro Met Lys
            260                 265                 270

Ala Leu Ile Asn Gly Cys Pro Glu Pro Leu Glu Ile Ala Asp Ala Gly
        275                 280                 285

His Phe Val Gln Glu Phe Gly Glu Gln Val Ala Arg Glu Ala Leu Lys
    290                 295                 300

His Phe Ala Glu Thr Glu Glx
305                 310
```

<210> SEQ ID NO 2
<211> LENGTH: 254
<212> TYPE: PRT
<213> ORGANISM: Xanthobacter autotrophicus

<400> SEQUENCE: 2

```
Met Ile Lys Ala Val Val Phe Asp Ala Tyr Gly Thr Leu Phe Asp Val
  1               5                  10                  15

Gln Ser Val Ala Asp Ala Thr Glu Arg Ala Tyr Pro Gly Arg Gly Glu
             20                  25                  30

Tyr Ile Thr Gln Val Trp Arg Gln Lys Gln Leu Glu Tyr Ser Trp Leu
         35                  40                  45
```

```
Arg Ala Leu Met Gly Arg Tyr Ala Asp Phe Trp Gly Val Thr Arg Glu
         50                  55                  60

Ala Leu Ala Tyr Thr Leu Gly Thr Leu Gly Leu Glu Pro Asp Glu Ser
 65                  70                  75                  80

Phe Leu Ala Gly Met Ala Gln Ala Tyr Asn Arg Leu Thr Pro Tyr Pro
                 85                  90                  95

Asp Ala Ala Gln Cys Leu Ala Glu Leu Ala Pro Leu Lys Arg Ala Ile
                100                 105                 110

Leu Ser Asn Gly Ala Pro Asp Met Leu Gln Ala Leu Val Ala Asn Ala
            115                 120                 125

Gly Leu Thr Asp Ser Phe Asp Ala Val Ile Ser Val Asp Ala Lys Arg
        130                 135                 140

Val Phe Lys Pro His Pro Asp Ser Tyr Ala Leu Val Glu Glu Val Leu
145                 150                 155                 160

Gly Val Thr Pro Ala Glu Val Leu Phe Val Ser Ser Asn Gly Phe Asp
                165                 170                 175

Val Gly Gly Ala Lys Asn Phe Gly Phe Ser Val Ala Arg Val Ala Arg
            180                 185                 190

Leu Ser Gln Glu Ala Leu Ala Arg Glu Leu Val Ser Gly Thr Ile Ala
        195                 200                 205

Pro Leu Thr Met Phe Lys Ala Leu Arg Met Arg Glu Glu Thr Tyr Ala
    210                 215                 220

Glu Ala Pro Asp Phe Val Val Pro Ala Leu Gly Asp Leu Pro Arg Leu
225                 230                 235                 240

Val Arg Gly Met Ala Gly Ala His Leu Ala Pro Ala Val Glx
                245                 250

<210> SEQ ID NO 3
<211> LENGTH: 933
<212> TYPE: DNA
<213> ORGANISM: Xanthobacter autotrophicus

<400> SEQUENCE: 3
atgataaatg caattcgcac cccggaccaa cgcttcagca atctcgatca gtatccgttc      60
agccccaact acctggacga cctccccggc tacccgggat tgcgggcaca ctacctcgac     120
gagggcaatt ctgacgctga agacgttttt ctctgccttc atggcgagcc cacctggagt     180
tacctgtatc gcaagatgat cccggtattt gctgaatcag gcgcacgagt tattgcgcca     240
gactttttgt gattcggaaa atccgacaag ccagtagacg aagaagacta caccttcgaa     300
tttcaccgca acttcctgct tgcactaatc gaacggcttg acttgcgcaa cattacgctg     360
gtcgttcagg actggggcgg atttttgggg ctgaccttac cgatggccga cccttcccgc     420
ttcaagcgcc tgatcatcat gaacgcctgc ttgatgaccg acccggtcac ccagcctgcg     480
tttagcgcct tgtcacccca gcctgcggat ggctttaccg cctggaaata cgatctggtt     540
acgccatcag acctgcgcct tgaccagttc atgaagcgtt gggcgcccac actgaccgaa     600
gctgaggcct ccgcgtatgc tgcgcctttc cctgacactt cctatcaggc tggtgtacgc     660
aagtttccca agatggtcgc gcaacgcgac caggcctgca tcgacatttc aaccgaagcg     720
atttcgttct ggcagaacga ctggaatggc cagaccttca tggccattgg catgaaagac     780
aaattgctgg accggacgt catgtatcct atgaaggcgc tcattaatgg ctgcccggaa     840
cccctcgaaa tagcggacgc tggccatttc gtacaggagt ttggcgagca agtggctcgc     900
gaggccctga acactttgc cgagacagaa tag                                   933
```

<210> SEQ ID NO 4
<211> LENGTH: 762
<212> TYPE: DNA
<213> ORGANISM: Xanthobacter autotrophicus

<400> SEQUENCE: 4

| | | | | | |
|---|---|---|---|---|---|
| atgatcaagg | cagtcgtgtt | cgacgcttac | ggtacgctct | tcgacgtcca | gtcggtggcc | 60 |
| gacgccaccg | agcgggcgta | tccaggccgg | ggcgagtaca | tcacgcaggt | ctggcggcag | 120 |
| aagcagctgg | aatacagctg | gctccgcgcg | ctgatggggc | gctatgccga | cttttggggc | 180 |
| gtcacgcggg | aagcgctggc | ctataccctc | ggaacgctgg | ggctggagcc | ggacgagtcc | 240 |
| ttcctcgccg | ggatggcgca | ggcctacaac | cgcctcacgc | cctatccgga | cgccgcgcaa | 300 |
| tgcctcgcgg | agctggcgcc | cctcaagcgc | gccatcctct | ccaacggcgc | gcccgacatg | 360 |
| ctgcaggcgc | tcgtggccaa | tgcgggcctg | acggacagct | tcgatgccgt | catcagcgtc | 420 |
| gatgccaagc | gcgtgttcaa | gcctcatccc | gactcctacg | cgctggtgga | ggaggtacta | 480 |
| ggcgtgacgc | ccgcggaggt | gctgttcgtg | tcctccaacg | gcttcgacgt | cggcggcgcg | 540 |
| aagaatttcg | gcttcagcgt | cgcccgggtc | gcgcgcctgt | cgcaggaggc | gctggcgcgc | 600 |
| gaactcgtct | cgggtaccat | cgcgcccctg | accatgttca | aggcgctgag | gatgcgggaa | 660 |
| gaaacctatg | cggaggcgcc | tgatttcgtg | gtgcccgccc | ttggcgacct | gccgcggctg | 720 |
| gttcgcggga | tggccggcgc | tcatctcgca | ccagcggtgt | ga | | 762 |

<210> SEQ ID NO 5
<211> LENGTH: 1371
<212> TYPE: DNA
<213> ORGANISM: Dehalobacter sp. CF

<400> SEQUENCE: 5

| | | | | | |
|---|---|---|---|---|---|
| atggacaagg | aaaaaagtaa | caacgataag | ccggcaacaa | aaattaatcg | cagacaattc | 60 |
| cttaaatttg | gagctggagc | ttcttcgggt | attgcaattg | ccactgcagc | tactgcattg | 120 |
| ggagggaaat | cacttatcga | tcccaaacag | gtatatgctg | gaacggtcaa | ggaactggat | 180 |
| gaacttccct | taatatccc | ggcagactac | aaaccgttta | ccaatcaaag | gaatatatat | 240 |
| ggccaggctg | tatgggagt | acccgaacct | ctagcacttg | tagagcgttt | tgatgaagta | 300 |
| agatggaatg | gttggcagac | agatggttcg | cccggtctta | ctgtacttga | tggtgcggct | 360 |
| gctcgtgcaa | gctttgccgt | tgattattat | tttaacgggg | aaaatagcgc | ctgcagggcc | 420 |
| aataaaggtt | tttttgaatg | gcatcccaaa | gtggccgagc | tgaactttaa | gtggggcgat | 480 |
| ccggagagaa | atattcattc | ccccggtgta | aaaagtgccg | aagaaggaac | gatggcagta | 540 |
| aaaaaaatag | ctagattttt | cggcgctgct | aaagctggga | tagcgccttt | tgacaaacgt | 600 |
| tgggtttta | ctgaaacgta | tgcctttgtt | aaaacgcctg | agggtgaaag | tctgaaattt | 660 |
| atccctccgg | attttgggtt | tgagcccaag | catgtaatct | cgatgattat | cccacagtcg | 720 |
| ccagaaggag | taaagtgtga | cccgtccttt | ttaggatcaa | ctgaatatgg | attaagttgt | 780 |
| gcccagattg | gatatgctgc | attcggttta | tccatgttta | ttaaagatct | gggatatcat | 840 |
| gcggttccaa | tcggatctga | cagtgcatta | gctataccta | tagctattca | ggcgggtctg | 900 |
| ggggaataca | gcaggtcggg | gctaatgatt | acgcctgaat | ttggttcaaa | tgttagactc | 960 |
| tgtgaagtat | ttactgacat | gcctttaaat | catgataaac | ctatttcatt | cggagtaact | 1020 |
| gaattttgca | aaacctgcaa | aaaatgcgct | gaagcatgcg | cccctcaagc | tattagctat | 1080 |

-continued

```
gaagatccta ccattgatgg acctcgtggg caaatgcaaa attcgggaat aaagagatgg    1140
tatgttgacc cggtgaagtg cttagaattc atgtcgcgtg ataacgtcgg aaactgctgc    1200
ggagcttgta tagctgcttg cccatttact aagccggaag cctggcacca taccttaatt    1260
aggagtctag taggagcacc tgttattact ccattcatga agatatggga tgatattttt    1320
ggatacggaa agctgaatga tgaaaaagcg atagcagatt ggtggaaata a             1371
```

<210> SEQ ID NO 6
<211> LENGTH: 456
<212> TYPE: PRT
<213> ORGANISM: Dehalobacter sp. CF

<400> SEQUENCE: 6

```
Met Asp Lys Glu Lys Ser Asn Asn Asp Lys Pro Ala Thr Lys Ile Asn
  1               5                  10                  15

Arg Arg Gln Phe Leu Lys Phe Gly Ala Gly Ala Ser Ser Gly Ile Ala
             20                  25                  30

Ile Ala Thr Ala Ala Thr Ala Leu Gly Gly Lys Ser Leu Ile Asp Pro
         35                  40                  45

Lys Gln Val Tyr Ala Gly Thr Val Lys Glu Leu Asp Glu Leu Pro Phe
     50                  55                  60

Asn Ile Pro Ala Asp Tyr Lys Pro Phe Thr Asn Gln Arg Asn Ile Tyr
 65                  70                  75                  80

Gly Gln Ala Val Leu Gly Val Pro Glu Pro Leu Ala Leu Val Glu Arg
                 85                  90                  95

Phe Asp Glu Val Arg Trp Asn Gly Trp Gln Thr Asp Gly Ser Pro Gly
            100                 105                 110

Leu Thr Val Leu Asp Gly Ala Ala Ala Arg Ala Ser Phe Ala Val Asp
        115                 120                 125

Tyr Tyr Phe Asn Gly Glu Asn Ser Ala Cys Arg Ala Asn Lys Gly Phe
    130                 135                 140

Phe Glu Trp His Pro Lys Val Ala Glu Leu Asn Phe Lys Trp Gly Asp
145                 150                 155                 160

Pro Glu Arg Asn Ile His Ser Pro Gly Val Lys Ser Ala Glu Glu Gly
                165                 170                 175

Thr Met Ala Val Lys Lys Ile Ala Arg Phe Phe Gly Ala Ala Lys Ala
            180                 185                 190

Gly Ile Ala Pro Phe Asp Lys Arg Trp Val Phe Thr Glu Thr Tyr Ala
        195                 200                 205

Phe Val Lys Thr Pro Glu Gly Glu Ser Leu Lys Phe Ile Pro Pro Asp
    210                 215                 220

Phe Gly Phe Glu Pro Lys His Val Ile Ser Met Ile Ile Pro Gln Ser
225                 230                 235                 240

Pro Glu Gly Val Lys Cys Asp Pro Ser Phe Leu Gly Ser Thr Glu Tyr
                245                 250                 255

Gly Leu Ser Cys Ala Gln Ile Gly Tyr Ala Ala Phe Gly Leu Ser Met
            260                 265                 270

Phe Ile Lys Asp Leu Gly Tyr His Ala Val Pro Ile Gly Ser Asp Ser
        275                 280                 285

Ala Leu Ala Ile Pro Ile Ala Ile Gln Ala Gly Leu Gly Glu Tyr Ser
    290                 295                 300

Arg Ser Gly Leu Met Ile Thr Pro Glu Phe Gly Ser Asn Val Arg Leu
305                 310                 315                 320

Cys Glu Val Phe Thr Asp Met Pro Leu Asn His Asp Lys Pro Ile Ser
```

```
                  325                 330                 335
Phe Gly Val Thr Glu Phe Cys Lys Thr Cys Lys Lys Cys Ala Glu Ala
                340                 345                 350

Cys Ala Pro Gln Ala Ile Ser Tyr Glu Asp Pro Thr Ile Asp Gly Pro
            355                 360                 365

Arg Gly Gln Met Gln Asn Ser Gly Ile Lys Arg Trp Tyr Val Asp Pro
        370                 375                 380

Val Lys Cys Leu Glu Phe Met Ser Arg Asp Asn Val Gly Asn Cys Cys
385                 390                 395                 400

Gly Ala Cys Ile Ala Ala Cys Pro Phe Thr Lys Pro Glu Ala Trp His
                405                 410                 415

His Thr Leu Ile Arg Ser Leu Val Gly Ala Pro Val Ile Thr Pro Phe
                420                 425                 430

Met Lys Asp Met Asp Ile Phe Gly Tyr Gly Lys Leu Asn Asp Glu
            435                 440                 445

Lys Ala Ile Ala Asp Trp Trp Lys
    450                 455

<210> SEQ ID NO 7
<211> LENGTH: 38
<212> TYPE: DNA
<213> ORGANISM: Artificial Sequence
<220> FEATURE:
<223> OTHER INFORMATION: primer

<400> SEQUENCE: 7
gacgcttacg gaggctctat gataaatgca attcgcac                              38

<210> SEQ ID NO 8
<211> LENGTH: 36
<212> TYPE: DNA
<213> ORGANISM: Artificial Sequence
<220> FEATURE:
<223> OTHER INFORMATION: primer

<400> SEQUENCE: 8
tggcagttcc ctactctcct attctgtctc ggcaaa                                36

<210> SEQ ID NO 9
<211> LENGTH: 3914
<212> TYPE: DNA
<213> ORGANISM: Artificial Sequence
<220> FEATURE:
<223> OTHER INFORMATION: Synthetic pTSa_DhlA vector

<400> SEQUENCE: 9
ataaaacgaa aggctcagtc gaaagactgg gcctttcgtt ttatctgttg tttgtcggtg      60
aacgctctcc tgagtaggac aaatccgccg ggagcggatt tgaacgttgc gaagcaacgg     120
cccggagggt ggcgggcagg acgcccgcca taaactgcca ggcatcaaat taagcagaag     180
gccatcctga cggatggcct ttttggaatt cagccagcaa gacagcgata gagggtagtt     240
atccacgtga aaccgctaat gccccgcaaa gccttgattc acggggcttt ccggcccgct     300
ccaaaaacta tccacgtgaa atcgctaatc agggtacgtg aaatcgctaa tcggagtacg     360
tgaaatcgct aataaggtca cgtgaaatcg ctaatcaaaa aggcacgtga aacgctaat     420 agccccttca gatcaacagc ttgcaaacac ccctcgctcc ggcaagtagt tacagcaagt     480
agtatgttca attagctttt caattatgaa tatatatatc aattattggt cgcccttggc     540
ttgtggacaa tgcgctacgc gcaccggctc cgcccgtgga caaccgcaag cggttgccca     600
```

```
ccgtcgagcg ccagcgcctt tgcccacaac ccggcggccg gccgcaacag atcgttttat      660 aaatttttt ttttgaaaaa gaaaagccc gaaaggcggc aacctctcgg gcttctggat       720
ttccgatcac ctgtaagtcg gacgaattcg gcgctcttcc gcttcctcgc tcactgactc     780
gctgcgctcg gtcgttcggc tgcggcgagc ggtatcagct cactcaaagg cggtaatacg     840
gttatccaca gaatcagggg ataacgcagg aaagaacatg tgagcaaaag gccagcaaaa     900
ggccaggaac cgtaaaaagg ccgcgttgct ggcgtttttc cataggctcc gccccctga     960 cgagcatcac aaaaatcgac gctcaagtca gaggtggcga aacccgacag gactataaag    1020
ataccaggcg tttccccctg gaagctccct cgtgcgctct cctgttccga ccctgccgct    1080
taccggatac ctgtccgcct ttctcccttc gggaagcgtg gcgctttctc atagctcacg    1140
ctgtaggtat ctcagttcgg tgtaggtcgt tcgctccaag ctgggctgtg tgcacgaacc    1200
ccccgttcag cccgaccgct gcgccttatc cggtaactat cgtcttgagt ccaacccggt    1260
aagacacgac ttatcgccac tggcagcagc cactggtaac aggattagca gagcgaggta    1320
tgtaggcggt gctacagagt tcttgaagtg gtggcctaac tacggctaca ctagaagaac    1380
agcatttggt atctgcgctc tgctgaagcc agttaccttc ggaaaaagag ttggtagctc    1440
ttgatccggc aaacaaacca ccgctggtag cggtggtttt tttgtttgca agcagcagat    1500
tacgcgcaga aaaaaggat ctcaagaaga tcctttgatc ttttctacgg ggtctgacgc    1560
tcagtggaac gaaaactcac gttaattctc atgtttgaca gcttatcatc gataagcttt    1620
aatgcggtag tttatcacag ttaaattgct aacgcagtca ggcaccgtgt atgaaatcta    1680
acaatgcgct catcgtcatc ctcggcaccg tcaccctgga tgctgtaggc ataggcttgg    1740
ttatgccggt actgccgggc ctcttgcggg atatcgtcca ttccgacagc atcgccagtc    1800
actatggcgt gctgctagcg ctatatgcgt tgatgcaatt tctatgcgca cccgttctcg    1860
gagcactgtc cgaccgcttt ggccgccgcc cagtcctgct cgcttcgcta cttggagcca    1920
ctatcgacta cgcgatcatg gcgaccacac ccgtcctgtg gatcctctac gccggacgca    1980
tcgtggccgg catcaccggc gccacaggtg cggttgctgg cgcctatatc gccgacatca    2040
ccgatgggga agatcgggct cgccacttcg gctcatgag cgcttgtttc ggcgtgggta    2100
tggtggcagg ccccgtggcc ggggactgt tgggcgccat ctccttgcat gcaccattcc    2160
ttgcggcggc ggtgctcaac ggcctcaacc tactactggg ctgcttccta atgcaggagt    2220
cgcataaggg agagcgtcga ccgatgccct tgagagcctt caacccagtc agctccttcc    2280
ggtgggcgcg gggcatgact atcgtcgccg cacttatgac tgtcttcttt atcatgcaac    2340
tcgtaggaca ggtgccggca gcgctctggg tcattttcgg cgaggaccgc tttcgctgga    2400
gcgcgacgat gatcggcctg tcgcttgcgg tattcggaat cttgcacgcc ctcgctcaag    2460
ccttcgtcac tggtcccgcc accaaacgtt tcggcgagaa gcaggccatt atcgccggca    2520
tggcggccga cgcgctgggc tacgtcttgc tggcgttcgc gacgcgaggc tggatggcct    2580
tccccattat gattcttctc gcttccggcg gcatcgggat gcccgcgttg caggccatgc    2640
tgtccaggca ggtagatgac gaccatcagg gacagcttca aggatcgctc gcggctctta    2700
ccagcctaac ttcgatcact ggaccgctga tcgtcacggc gatttatgcc gcctcggcga    2760
gcacatggaa cgggttggca tggattgtag gcgccgccct ataccttgtc tgcctccccg    2820
cgttgcgtcg cggtgcatgg agccgggcca cctcgacctg aatggaagcc ggcggcacct    2880
cgctaacgga ttcaccactc ttgacattgt aggtcaggcg acctactttg tcattgctag    2940
```

-continued

```
gtcacccgac ctaactttttg acagacgctt acggaggctc tatgataaat gcaattcgca  3000
ccccggacca acgcttcagc aatctcgatc agtatccgtt cagccccaac tacctggacg  3060
acctccccgg ctacccggga ttgcgggcac actacctcga cgagggcaat tctgacgctg  3120
aagacgtttt tctctgcctt catggcgagc ccacctggag ttacctgtat cgcaagatga  3180
tcccggtatt tgctgaatca ggcgcacgag ttattgcgcc agactttttt ggattcggaa  3240
aatccgacaa gccagtagac gaagaagact acaccttcga atttcaccgc aacttcctgc  3300
ttgcactaat cgaacggctt gacttgcgca acattacgct ggtcgttcag gactggggcg  3360
gatttttggg gctgaccta ccgatggccg acccttcccg cttcaagcgc ctgatcatca  3420
tgaacgcctg cttgatgacc gacccggtca cccagcctgc gtttagcgcc tttgtcaccc  3480
agcctgcgga tggctttacc gcctggaaat acgatctggt tacgccatca gacctgcgcc  3540
ttgaccagtt catgaagcgt tgggcgccca cactgaccga agctgaggcc tccgcgtatg  3600
ctgcgccttt ccctgacact tcctatcagg ctggtgtacg caagtttccc aagatggtcg  3660
cgcaacgcga ccaggcctgc atcgacattt caaccgaagc gatttcgttc tggcagaacg  3720
actggaatgg ccagaccttc atggccattg gcatgaaaga caaattgctg ggaccggacg  3780
tcatgtatcc tatgaaggcg ctcattaatg gctgcccgga accctcgaa atagcggacg  3840
ctggccattt cgtacaggag tttggcgagc aagtggctcg cgaggccctg aaacactttg  3900
ccgagacaga atag                                                     3914
```